(12) United States Patent
Müller et al.

(10) Patent No.: US 6,561,005 B2
(45) Date of Patent: May 13, 2003

(54) PROCEDURE AND DEVICE FOR ACOUSTICALLY DETECTING MICROPARTICLES

(75) Inventors: Martin Müller, Berlin (DE); Rudolf Germer, Berlin (DE); Markus Kalkum, Bonn (DE); Holger Eickhoff, Berlin (DE)

(73) Assignee: Max-Planck-Gesellschaft zur Forderung (DE)

( * ) Notice: Subject to any disclaimer, the term of this patent is extended or adjusted under 35 U.S.C. 154(b) by 0 days.

(21) Appl. No.: 09/755,742

(22) Filed: Jan. 5, 2001

(65) Prior Publication Data

US 2001/0007210 A1 Jul. 12, 2001

(30) Foreign Application Priority Data

Jan. 10, 2000 (DE) ......................................... 100 00 608

(51) Int. Cl.[7] .............................................. G01P 25/00
(52) U.S. Cl. .................... 73/1.74; 73/432.1; 73/861.27
(58) Field of Search .................. 73/579, 580, 1.16, 73/1.25, 1.26, 1.74, 12.01, 12.04, 12.05, 12.07, 12.11, 61.75, 61.79, 861.04, 861.18, 861.21, 861.27, 861.73, 597–600, 432.1

(56) References Cited

U.S. PATENT DOCUMENTS

| | | | | |
|---|---|---|---|---|
| 3,653,253 A | * | 4/1972 | Olin ........................... 310/328 |
| 3,844,174 A | * | 10/1974 | Chabre ....................... 310/312 |
| 4,041,768 A | * | 8/1977 | Gibert et al. ............... 73/24.03 |
| 4,265,107 A | * | 5/1981 | Cheng et al. ............... 73/28.05 |
| 4,651,331 A | * | 3/1987 | Harrsen et al. ................ 377/6 |
| 4,869,722 A | * | 9/1989 | Heyman ..................... 604/253 |
| 5,257,530 A | * | 11/1993 | Beattie et al. ............. 73/61.75 |
| 5,419,176 A | * | 5/1995 | Walker ....................... 73/12.05 |
| 5,681,986 A | * | 10/1997 | Merk et al. .................. 310/337 |

FOREIGN PATENT DOCUMENTS

| | | | |
|---|---|---|---|
| DE | OS 29 37 709 A1 | 9/1981 | |
| DE | 298 20 546 U1 | 3/1999 | |
| EP | 0 482 750 A1 | 4/1991 | |
| JP | 2000-79679 A | * 3/2000 | ............. B41J/2/01 |
| WO | WO 99/27372 | 6/1999 | |

\* cited by examiner

*Primary Examiner*—Hezron Williams
*Assistant Examiner*—Rose M. Miller
(74) *Attorney, Agent, or Firm*—Cook, Alex, McFarron, Manzo, Cummings & Mehler, Ltd.

(57) ABSTRACT

A procedure for detecting microparticles released by at least one dispenser, encompassing the following steps: (a) triggering the dispenser over an oscillation target (20) with a sensor material (21), so that at least one microparticle hits the sensor material (21) and excites an acoustic wave, (b) detecting the acoustic wave with at least one oscillation sensor (31) connected with the sensor material (21), which emits an electrical sensor signal when the acoustic wave arrives, and (c) evaluating the sensor signal to determine the impact of the microparticle. The procedure is aimed at detecting the impact and/or impact positions of microparticles on a target. A detector for executing the procedure is also described.

22 Claims, 2 Drawing Sheets ue: 6,561,005 B2

PROCEDURE AND DEVICE FOR ACOUSTICALLY DETECTING MICROPARTICLES

FIELD OF THE INVENTION

The invention relates to a procedure for acoustically detecting microparticles, in particular for determining the appearance and/or positions of dispensed microparticles or for detecting the orientations of dispensers of a microparticle dispensing head, in particular for calibrating dispenser heads. The invention also relates to a procedure for executing such procedures, in particular to a detector for detecting the impact and/or impact position of microparticles released from a dispenser head.

TECHNICAL BACKGROUND

It is generally known to place the smallest amounts of solid and/or liquid substances on a substrate with a microdispenser in the form of drops or solid particles (hereinafter generally referred to as microparticles). The microdispenser is used to apply defined volumes on the substrate at predetermined positions. A microdispenser can have a dispenser head with several dispensers, for example to position various substances on the substrate.

The microparticles released by a dispenser are generally so small that the function of a dispenser cannot be visually checked either qualitatively or quantitatively. However, malfunctions are extremely disadvantageous, since samples or reactants might inadvertently not be made to interact on substrates in the desired manner, for example during applications in biotechnology and genetic engineering. Therefore, there is interest in having a reliable measuring system with which the microparticles released by dispensers can be recorded.

There is also an interest in placing the samples or reactants on substrates with an extremely high surface density for the mentioned applications in biotechnology and genetic engineering. In addition to high accuracy and reproducibility for dispenser head positioning, this also requires knowledge of where the dispensed microparticles impact the substrate. Experience shows that the relative positions of the impact points do not correlate with the relative positions of the dispensers on the dispenser head. PCT/EP98/07559 describes this problem and various techniques for its resolution.

In earlier optical dispenser head calibrations performed with stroboscopic procedures, a new calibration principle was established by the technique underlying Patent Application PCT/EP98/07558. In this case, a dispenser head is repeatedly traversed over an optical or electroacoustic interaction area with linear borders while microparticles are released, and the impact of dispensed microparticles on the borders is detected. The impact times and geometric properties of the linear borders are used to determine the relative impact positions of the individual dispensers. This calibration technique offers the advantages of complete automation, high speed and reliability. However, the disadvantage to this technique is that the dispenser head must be repeatedly moved, or the accompanying system of coordinates must be activated repeatedly. In addition to the accuracy, this restricts primarily the speed of calibration.

There is interest in increasing the surface density of the samples applied to a substrate. This placed higher demands in particular on the accuracy of the dispensing head calibration.

SUMMARY OF THE INVENTION

The object of the invention is to indicate an improved procedure for microparticle detection, with which disposed microparticles can be recorded and/or localized at a higher rate and precision, and in particular which enables a functional check and/or calibration of dispenser head with an elevated accuracy and reproducibility. The object of the invention is also to indicate a detector for executing the mentioned procedure.

The invention is based on the idea of acoustically detecting the impact of a dispensed microparticle on a sensor target by having the microparticle impacting a sensor material (e.g., sensor film) of the sensor target trigger an acoustic wave that is detected with at least one sound converter. Depending on the application, the electric sound converter signal is evaluated only relative to the recording (detecting) of the microparticle or its localization.

In order to localize the microparticle, is it provided that the impact point (impact position) of at least one dispensed microparticle released by at least one dispenser be determined from the differences in run times required by an acoustic wave excited by the microparticles on the sensor material (e.g., stepped up sensor film) to pass from the impact position along at least three different predetermined paths to at least one oscillation or sound sensor (sound converter).

In a first embodiment of the invention aimed only at recording a dispensed microparticle, the acoustic wave is detected with at least one oscillation sensor connected with the sensor material, whose electrical sensor signal is evaluated for detecting the impact of the microparticle. To this end, the sensor signal is compared with a predetermined impact signal.

In a second embodiment of the invention also aimed at localizing a dispensed microparticle, the mentioned three paths are formed by a combination of at least two reflector elements and at least one oscillation sensor (or at least one reflector element and at least two oscillation sensors) on the sensor material (sensor film). The paths are the straight paths from the impact point directly to the oscillation sensor or from the impact point via the reflector elements to the oscillation sensor. In a third embodiment, at least three oscillation sensors are provided on the sensor material for particle localization. At least three straight paths are formed by the paths from the impact point directly to a respective oscillation sensor. The third embodiment is preferred due to a simplified setup and simplified signal evaluation.

The impact positions are determined from the run time differences as an absolute calculation, taking into account the known lengths of the paths and speeds of the acoustic waves, or as a relative determination by comparing the run time differences determined with various dispensers. In particular, the invention provides that the relative impact positions of dispensed microparticles from various dispensers of a dispenser head be determined by ascertaining reference run time differences for a reference dispenser of the dispenser head, and correlating the measured run time differences with the reference run time differences for all other dispensers of the dispensing head, and determining the relative impact positions from this.

The run time differences are preferably measured using a simple counting technique, for example by having one of the oscillation sensors where the surface wave is first detected emit a start signal to a counter, and having the remaining oscillation sensors emit a read signal to the counter on detection of the surface wave. The count differences each corresponding to the start and read signals are determined, and the run time differences are determined from this. The impact positions can be directly derived from the count differences. If a high-frequency counter module (counting rate in MHz range) is used as the counter, impact positions can be determined to within μm accuracy.

Depending on the size of the oscillation target with the sensor material (sensor film or sensor film), the acoustic signals supplied following the impact of a microparticle can be determined for all dispensers of a dispenser head simultaneously, or for the individual dispensers in sequence (alternating with an adjustment movement of the dispenser head).

In particular, a detector according to the invention exhibits an oscillation target with a sensor material (especially with a clamped-on sensor film), with which reflector elements and at least one oscillation sensor are connected, depending on the embodiment. The oscillation sensors, which are preferably formed by capacitor microphones with oscillation couplers, or the reflector elements are spaced apart from each other.

According to a further preferred embodiment, the sensor foil is made from a piezoelectric material (piezoelectric foil). The oscillation sensors are formed by metallic layers which are deposited at predetermined positions on the foil. The metallic layers on the piezoelectric material fulfill the function of the above mentioned microphones.

The invention offers the following advantages. Microparticle detection according to the invention provides a direct monitoring and validation of dispenser function, e.g., during the manufacture of microdispensed substance grids. A robust, fast, highly precise and easily automatable dispenser head calibration is also enabled. The dispenser head to be calibrated does not have to be repeatedly moved over the oscillation target according to a specific path. It is enough to reproducibly set the dispenser as desired relative to the sensor film. While the dispensing procedure is in progress, the dispenser head must be moved. The relative positions of the impact points of dispensed microparticles can be determined with an accuracy of roughly 10 μm (or under down to the 100 nm range). The acoustic particle detection takes place with a minimal evaluation time.

BRIEF DESCRIPTION OF THE DRAWINGS

Additional advantages and details of the invention can be gleaned from the description of the attached drawings. Shown on.

PREFERRED EMBODIMENTS

The invention will be described below in relation to the setup of a detector for microparticle detection and procedures for their use. The design of the used dispensers and type of dispensed microparticles will not be described. The invention can be used with all known dispenser types, in particular with individual dispensers or with dispenser heads with numerous dispensers arranged in rows or in a matrix. The dispensers can be any types of arrangements for the vertical, horizontal or otherwise inclined release of microparticles, e.g., piezoelectrically, electromechanically or hydrodynamically actuated micropipettes, or micro-drop firing devices that operate like ink jet printers. Typical volumes for the dispersed microparticles lie at roughly 100 pl. In addition, the drivers and controllers known for the dispenser(s) will not be described in detail. A dispenser or dispenser head is typically moved with an x-y-z actuator, which can be connected with the signal evaluation circuit of the detector according to the invention (see below).

Figure 1:
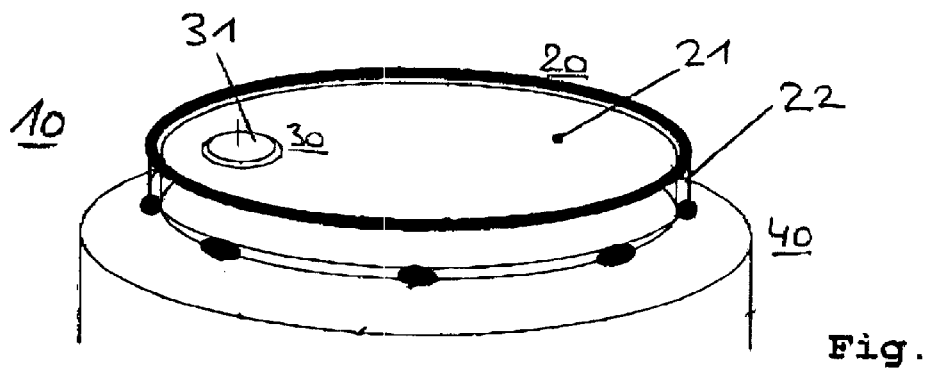
FIG. 1 is a diagrammatic perspective view of a first embodiment of a detector according to the invention.

The first embodiment mentioned above (particle recording) of the detector 10 according to the invention is diagrammatically shown on FIG. 1. It comprises an oscillation target 20 with a flat sensor material 21, a sound converter 30 and a carrier 40. The flat sensor material is formed by a clamped-on sensor film. Use of the sensor film is not a compulsory feature of the invention. As an alternative, another layer or volume material can be provided to form a free surface as the target for the microparticles. The free surface is preferably larger than the typical lateral expansion of the dispenser on the dispenser head. However, the sensor film is preferred in this embodiment and the ones described below due to the relatively low running speeds of excited acoustic waves. Preferably, the sensor film (or sensor foil) has a thickness in the range below 100 μm, preferably below 20 μm. With decreasing film thickness the sound velocity (running speed of acoustic waves) decreases. Accordingly, the run times are growing allowing an improvement of the sensor resolution. The sound converter 30 has only one sensor 31.

The embodiment according to FIG. 1 is used for particle recording. A microparticle impacting the surface of the sensor film triggers a sensor signal at the sensor 31, and the signal is processed with an evaluation circuit described below with reference to FIG. 7. Details of the oscillation target 20, the sound converter 30 and the carrier 40 are set up as described in the following embodiment.

Figure 2:
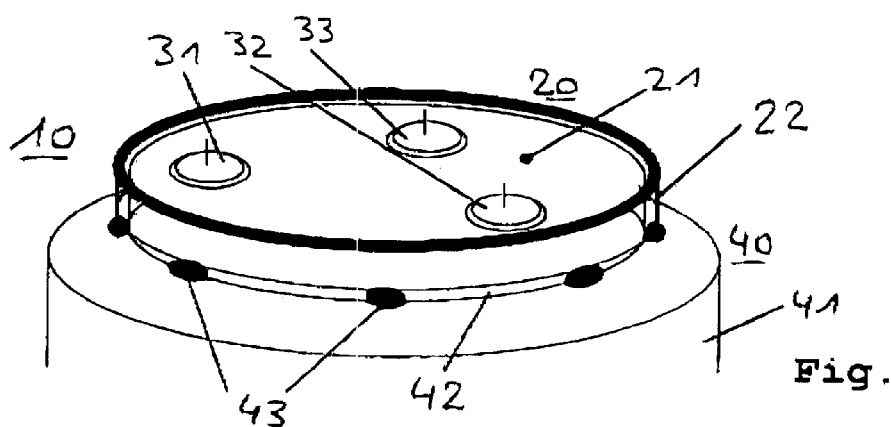
FIG. 2 is a diagrammatic perspective view of another embodiment of a detector according to the invention.
Figure 3:
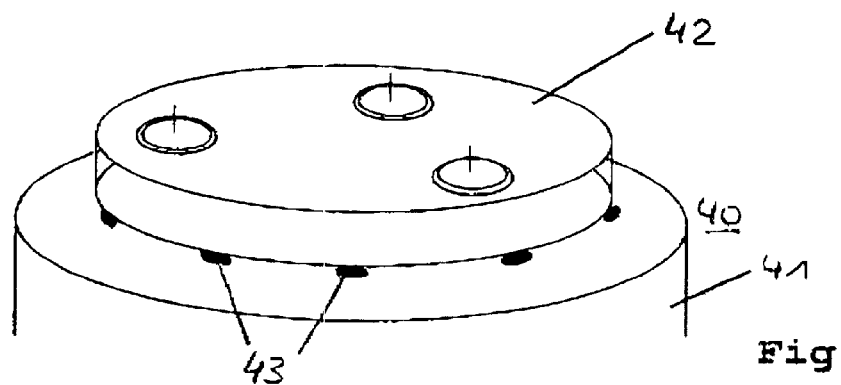
FIG. 3 is a diagrammatic perspective view of the detector according to FIG. 2 with oscillation target removed.
Figure 4:
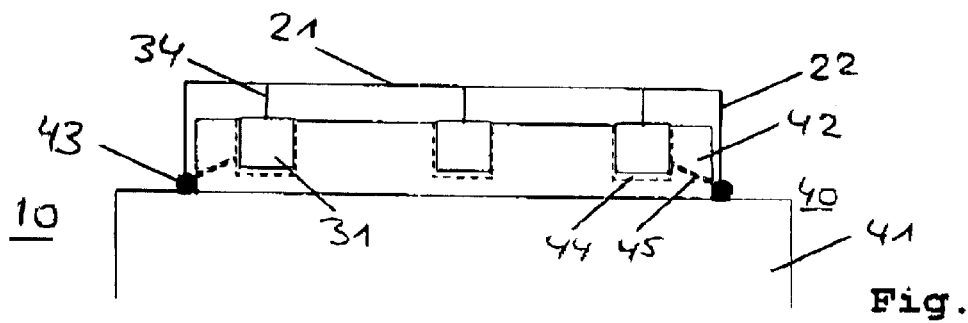
FIG. 4 is a diagrammatic sectional view of the detector according to FIG. 2, FIGS. 5, 6 are diagrammatic illustrations of the run time measurement according to the invention.

The third embodiment mentioned above (particle localization) of the detector 10 according to the invention is diagrammatically shown on FIGS. 2 to 4. It also exhibits an oscillation target 20, a sound converter 30 and a carrier 40. The detector 10 is called a drum sensor as the oscillation target 20 with the carrier 40 are shaped in the form of a drum with clamped-on drum skin. The second embodiment mentioned above shall be taken up further below.

The oscillation target 20 encompasses a sensor film 21, which is clamped on a frame 22 like a drum skin. The sensor film 21 is a thermal film with a thickness of 20 μm, for example, which is preferably shrunk onto the frame 22 tautly via heating with a specific tension force. The sensor film 21 consists of a polymer material. The frame 22 resembles a straight cylinder jacket. It consists of a rigid plastic material, e.g., PMMA, and has a wall thickness of approx. 1 mm and a height of approx. 5 mm. The diameter of the frame measures 35 mm, for example. A rotating collar surface can be provided at the top end of the frame 22 that carries the clamped-on sensor film (as shown in FIGS. 1, 2) to improve adhesion of the sensor film 21 on the frame 22.

In the example shown, the sound converter 30 encompasses three capacitor microphones 31, 32 and 33, which are acoustically coupled with the sensor film 21. Each capacitor microphone (e.g., see 31 on FIG. 4) carries a coupling pin 34 for oscillation coupling with the sensor film 21, wherein the coupling pin is secured to the oscillating membrane of the capacitor microphone 31 one the one hand, and contacts the sensor film 21 on the other. The coupling pins 34 are formed by rigid or elastically deformable wires, for example. The coupling pins 34 are not a compulsory feature of the invention. Other forms of sound oscillation coupling between the sensor material 21 and sensors 31 can be provided (see below).

The carrier 40, shown on FIG. 3 without the oscillation target 20, encompasses a base block 41, a sensor holder 42 and spacer 43. The base block 41 consists of a compact PMMA cylinder, for example, with a tapered section provided at the top end to form the sensor holder 42. At the bottom end of the base block 41 (not shown), a carrier plate or other component of a laboratory table or adjustment device is provided, depending on the application. In the example shown, the base block 41 has a diameter of approx. 45 mm. The sensor holder 42 has a height of 8 mm, and a diameter of approx. 30 mm. The edge formed by the tapered sensor holder 42 at the end of the base block 41 has adjustable spacers 43. The spacers 43 can consist of a plastically deformable plastic compound (e.g., kneadable silicon balls) as shown, or take the form of a mechanical height adjustment (not shown). The mechanical height adjustment can be achieved by a group of adjustable fine-threaded carrier elements, or by interacting female and male threads on the frame 22 or sensor holder 42. The spacers are used to adjust the oscillation target 20 relative to the sensor holder 42, in particular to position the sensor film 21 in such a way that it is contacted by the coupling pins 34 of the microphone under a minimal force exposure.

The sensor holder 42 has recesses 44 for each microphone 31, 32 or 33, in which a capacitor microphone is arranged at least partially recessed and oscillation-damped. For purposes of oscillation damping, the recesses 44 have foam layers (not shown), for example. A channel 45 extends from each recess 44 through the body of the sensor holder 42. The channels 45 accommodate the electrical connecting lines of the sound converter. The microphones are arranged in such a way that the coupling pins 34 project from the sensor holder 42.

To detect dispensed microparticles, the detector 10 is brought into the line of travel of a dispenser or dispenser head. At least one dispenser is positioned in such a way that a dispensed microparticle hits the sensor film 21. There are no limits with respect to the impact point. For reasons of measuring accuracy, however, an impact point within the triangle clamped on by the microphones 31 to 33 is preferred. A microparticle hitting the sensor film 21 (e.g., a microdrop with a volume of about 100 pl corresponding to a mass of about 100 ng) triggers an acoustic surface wave when it strikes the sensor film, which propagates in a circular fashion from the impact point outward. After a run time specific to the tension force and material, the surface wave first triggers a signal at a microphone located the closest to the impact point. In the microphones lying further away, a signal is released after correspondingly higher run times of the surface wave in the sensor film 21. The signals are generated by virtue of the fact that the surface wave is transferred via the coupling pins 34 to the microphone membrane, so that an electrical microphone signal is formed. Further processing of the electrical microphone signal will be described below drawing reference to FIG. 6.

Even though the detector according to the invention also enables an absolute determination of the impact positions for dispensed microparticles, a relative determination is preferably executed, as described below drawing reference to FIGS. 5 and 6.

Figure 5:
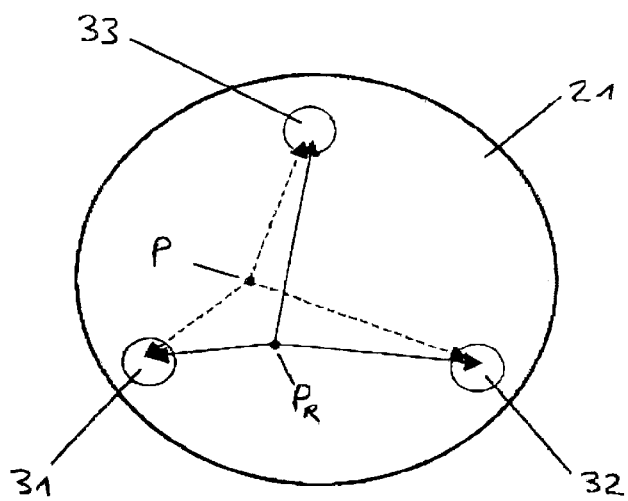
Figure 6:
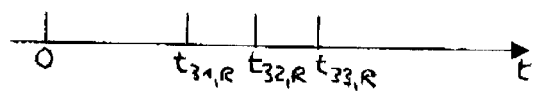

FIG. 5 shows the sensor films 21 with capacitor microphones 31 to 33 in a diagrammatic top view. To determine the impact position of a microparticle released from a specific dispenser of a dispenser head, a reference dispenser is first moved over the detector. The dispenser head is here in a specific reference position, which can be reproducibly adjusted with the control drive of the dispenser head. The microparticle released by the reference dispenser hits the sensor film 21 at $P_R$, for example. The surface wave emanating from PR first reaches the microphone 31, and subsequently microphones 32 and 33. The chronological formation of the microphone signal is illustrated in the top part of FIG. 6. After a start time (0), the surface wave arrives at the microphones at times $t_{31,R}$, $t_{32,R}$ or $t_{33,R}$. The absolute position of the start time 0 is of no concern for the ensuing measured value evaluation.

After run times $t_{31,R}$ to $t_{33,R}$ of the reference dispenser have been determined, the dispenser to be measured is moved over the detector. The corresponding position of the dispenser head is known from the predetermined setting of its control drive. The dispensed microparticle hits the sensor film 21 at P. The surface wave excited in the process runs along the dashed lines to the microphones. The corresponding run times are illustrated in the bottom part of FIG. 6. As evident, the surface wave first runs from the impact position P back to the microphone 31, then to the microphone 33 and finally to the microphone 32, depending on the times $t_{31}$, $t_{33}$ or $t_{32}$.

Since they are linearly correlated to the path differences from the impact positions $P_R$ to P to the microphones 31 to 33, the run time differences $t_{33,R}-t_{32,R}$ and $t_{32,R}-t_{31,R}$ or $t_{35}-t_{32}$ and $t_{32}-t_{31}$ make it possible to directly derive the relative position of P relative to $P_R$ and, taking into account the known positions of the dispenser head, to determine the relative positions of the accompanying dispensers.

Figure 7:
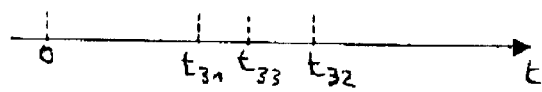
FIG. 7 is a block diagram of an evaluation circuit for recording particles according to the invention.
Figure 7:
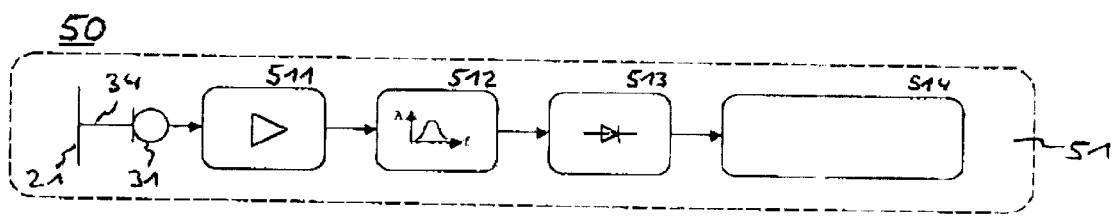
Figure 8:
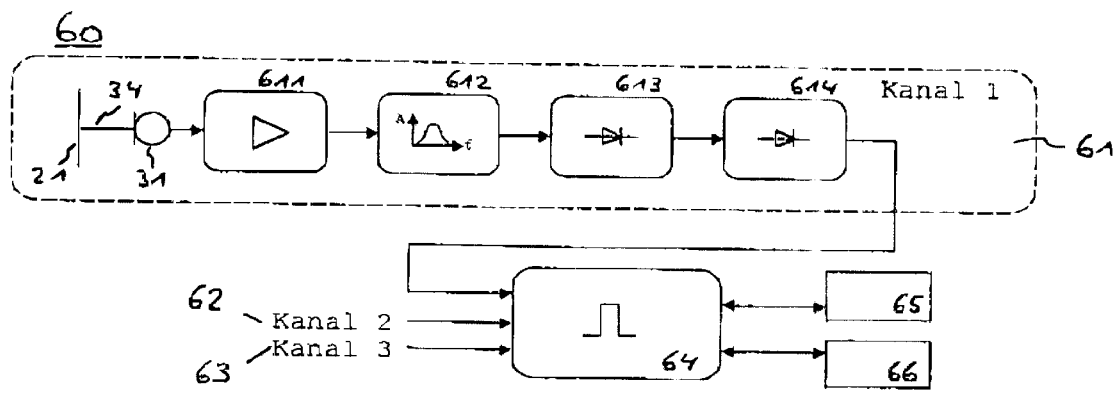
FIG. 8 is a block diagram of an evaluation circuit for localizing particles according to the invention.

FIGS. 7 and 8 illustrate evaluation circuits 50 and 60, which are designed for particle recording and localization.

Only one measuring channel is provided as the evaluation circuit 50 exclusively for particle recording (FIG. 7). The measuring channel 51 runs from the microphone 31, which is connected with the sensor film 21 by the coupling pin 34, through a preamplifier 511, a band pass 512 and rectifier 513 to a threshold value and comparison circuit 514, whose output is connected with an optical display or acoustic transducer, for example. The microphone signal is amplified by the amplifier 511, filtered with the band pass 512, then rectified with the rectifier 513 and compared with a predetermined reference impact signal (or reference signal range) with the threshold value and comparison circuit 514. The impact of a microdrop triggers a display signal at the output of the threshold value circuit 514 if the processed microphone signal matches the reference impact signal. The components 511 to 514 of the input channel 51 are designed in such a way that the display received a display signal trouble-free only if it receives a surface wave caused by a microparticle impact. The circuit 54 is essentially not influenced by other sound sources.

The shape and/or amplitude of the sensor signal can also be compared with the corresponding parameters of the characteristics impact signal, and the display signal can be modified accordingly. In addition, a classification (comparison with several impact signals) can be used to determine the mass of the registered microparticle from the amplitude of the sensor signal.

The run time measurement preferably takes place by means of a pulse count, which will be described below with reference to FIG. 8. FIG. 8 diagrammatically illustrates the setup of an evaluation circuit 60 for evaluating the microphone signals obtained with the detector 10. Each microphone is connected with a pulse generator and counter circuit 64 by means of an input channel. Of the three input channels 61 to 63, only the input channel 61 is shown in detail.

The input channel 61 runs from the microphone 31, which is connected with the sensor film 21 by the coupling pin 34, through a preamplifier 611, a band pass 612, a rectifier 613 and a threshold value circuit 614, whose output is connected with the pulse generator and counter circuit 64. After processed with circuits 611, 612 and 613 (as in FIG. 7), the microphone signal is adjusted to a TTL level with the threshold circuit 614. The impact of a microdrop triggers a positive 5 V edge at the output of the threshold circuit 614. Circuits 611 to 614 are again designed in such a way that the circuit 65 receives a start or read signal trouble-free only if it receives a surface wave generated by the impact of a microparticle.

If the surface wave generated by the microparticle impact reaches the microphone 31, a signal is triggered at the threshold value circuit 614 that immediately starts the pulse generator part of the circuit 64. The pulse generator part is preferably a quartz-stabilized generator with a base frequency in the MHz range. The base frequency measures 80 MHz, for example. As the base frequency increases, so too does the resolution of position determination. This stems from the following consideration. In the detector with the design described above, the running speed of a wave on the sensor film measures roughly 20 nm in 1 ms. The period at a counted pulse frequency of 80 MHz is roughly 12.5 ns or a path of roughly 230 nm. Correspondingly, the locational resolution theoretically lies in the 200 nm range. However, only larger distances can practically be resolved due to time fluctuations in the evaluation circuit (e.g., roughly 10 $\mu$m).

All subsequently arriving signals from the remaining microphones initiate a readout of the current count. Given three microphones, two numerical values (counts) are available, from which the run time differences (see FIG. 6) of the arriving signals can be directly derived.

The described acquisition of run time differences can be repeated for each dispenser of a dispenser head until all relative positions have been determined relative to the reference dispenser. During subsequent operation of the dispenser head for dispensing samples on substrates, the dispenser head drive is then actuated taking into account the relative positions of the individual dispensers. To this end, the dispenser head drive 65 is connected with the circuit 64 and a control computer 66 to evaluate the counts and determine the relative positions.

The detector described above can be modified in a variety of ways depending on the application, without departing from the principle according to the invention of acoustic particle acquisition or relative position determination from measuring run time differences. For example, it is possible to use more sound converters as sensors in place of three microphones. The microphones can also be comprised of microphone configurations other than capacitor microphones.

In addition, the sound converter 30 according to the aforementioned second embodiment can also consist of a combination of microphones and reflector elements at the edge of the sensor film 21, through which the corresponding paths from the impact positions to the microphone are defined.

Finally, the design of the deflector can also be modified relative to the used materials, shape and size of the sensor film. As an example, the sensor film can consist of a piezoelectric material. The thickness of the piezoelectric material preferably is in the range below 100 $\mu$m, e.g. 20 $\mu$m. The sound converters are formed by metallic layers being connected with the above data acquisition circuitry via electrical lines. The metallic layers are deposited in predetermined regions according to the positioning of the above microphones on one or both sides of the film. The deposition is preferably made by a lithographic procedure. This embodiment has the following particular advantages. The sound converters (metallic layers) can be positioned with high precision. Any particular measures for improving the sound coupling between the film and the converter can be avoided. A sensor according to the invention can be made with high reproducibility. Sensors can be replaced without calibration. Furthermore, a plurality of sound converters can be deposited on the piezoelectric film. The film preferably consists of a piezoelectric ceramic.

The detector can be designed as a manually adjustable hand-held machine. The dimensioning described above is intended for measurements with one dispenser, for example. Given a larger sensor film, all dispensers of a dispenser head can be arranged over the sensor film, and the described measurement can be performed without any movements, as illustrated below.

The dispenser head is oriented relative to the oscillation target in such a way that the microparticle existing each dispenser of the dispenser head would impact the sensor film. The individual dispensers are sequentially actuated for position acquisition. Each impacting microparticle excites a surface wave on the oscillation target, which is detected by the sound converters. Further measurement evaluation takes place according to the principles outlined above.

The features of the invention disclosed in the above description, drawings and claims can be of importance for realizing the invention is its various configurations, whether individually or in any combination.

What is claimed is:

1. A procedure for detecting microparticles released by at least one dispenser, with the following steps:

(a) triggering the dispenser over an oscillation target with a sensor material, so that at least one microparticle hits said sensor material and excites an acoustic wave, (b) detecting said acoustic wave with at least one oscillation sensor connected with said sensor material, said at least one oscillation sensor omitting an electrical sensor signal when said acoustic wave arrives, wherein differences in run times of said acoustic wave on at least three differently progressing paths to said at least one oscillation sensor are measured, and (c) evaluating said run time differences to determine the impact of said microparticle.

2. A procedure according to claim 1, in which step (c) involves recording a microparticle when the sensor signal corresponds to a characteristic impact signal.

3. A procedure according to claim 2, in which step (c) involves comparing the shape or amplitude of said sensor signal with the corresponding parameters of said characteristic impact signal.

4. A procedure according to claim 3, in which step (c) involves determining the mass of the recorded microparticles from the amplitude of the sensor signal.

5. A procedure according to claim 1, in which an impact position of at said least one microparticle released by said at least one dispenser is determined.

6. A procedure according to claim 5, in which the run time differences are measured by detecting said acoustic wave with a combination of reflector elements and said at least one oscillation sensor in step (b).

7. A procedure according to claim 5, in which the run time differences are measured by detecting said acoustic wave with at least three oscillation sensors spaced apart from each other.

8. A procedure according to claim 5, in which the impact position of said microparticle is determined in step (c) from the measured differences in run times and reference differences in run times measured during a reference measurement with a reference dispenser.

9. A procedure according to claim 7, in which the run time differences are measured by having one of said oscillation sensors where said acoustic wave was first detected relay a start signal to a counter, having the remaining oscillation sensors emit a read signal to said counter on detection of the acoustic wave, determining the differences in counts are according to the start and read signals, and determining the run time differences from that.

10. A procedure according to claim 9, in which a high-frequency counter component is used as the counter.

11. A device for detecting microparticles dispensed with a dispenser, comprising:
   an oscillation target having a flat oscillation material, whose upper side is exposed to impact by said microparticles,
   an oscillation detection arrangement with at least one microphone, said at least one microphone being coupled with said oscillation target, and
   the oscillation material encompasses a clamped-on sensor film.

12. A device according to claim 10, in which the oscillation detection arrangement has at least one microphone and at least two reflector elements spaced apart from each other.

13. A device according to claim 10, in which the oscillation detection arrangement has at least three microphones spaced apart from each other.

14. A device according to claim 10, in which the sensor film is applied with a frame over a carrier, on which said at least one microphone is positioned.

15. A device according to claim 14, in which the frame is height adjustably secured with spacers over the carrier.

16. A device according to claim 12, in which said at least one microphone is a capacitor microphone.

17. A device according to claim 13, in which each of said at least three microphone is connected with a pulse generator and counter circuit by way of an input channel.

18. A device according to claim 17, in which the pulse generator and counter circuit has a quartz-stabilized high-frequency generator.

19. A device according to claim 14, in which said carrier has a base block and a sensor holder, wherein the frame is secured on said base block, and the sensor holder has at least one recess, in which one microphone of said at least one microphone is secured in an oscillation damped manner.

20. A device according to claim 10, in which the sensor film consists of a piezoelectric material.

21. A device according to claim 20, in which the at least one oscillation sensor is formed by metallic layers formed on the piezoelectric material.

22. Procedure of recording and/or localizing dispensed microparticles, or subjecting a dispenser head to a functional check calibration, wherein a device according to claim 19 is used.

* * * * *

UNITED STATES PATENT AND TRADEMARK OFFICE
CERTIFICATE OF CORRECTION

PATENT NO.    : 6,561,005 B2
DATED         : May 13, 2003
INVENTOR(S)   : Martin Muller et al.

It is certified that error appears in the above-identified patent and that said Letters Patent is hereby corrected as shown below:

<u>Title page,</u>
Item [73], should read as follows:
-- [73] Assignee: Max-Planck-Gesellschaft zur Forderung der Wissenschaften e. V. --

Signed and Sealed this

Ninth Day of September, 2003

JAMES E. ROGAN
*Director of the United States Patent and Trademark Office*